(12) United States Patent
Bosio et al.

(10) Patent No.: US 11,866,729 B2
(45) Date of Patent: Jan. 9, 2024

(54) METHOD FOR THE GENERATION OF A CELL COMPOSITION VENTRAL MIDBRAIN PATTERNED DOPAMINERGIC PROGENITOR CELLS

(71) Applicant: Miltenyi Biotec B.V. & Co. KG, Bergisch Gladbach (DE)

(72) Inventors: Andreas Bosio, Cologne (DE); Andrej Smiyakin, Rösrath (DE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 449 days.

(21) Appl. No.: 17/011,746

(22) Filed: Sep. 3, 2020

(65) Prior Publication Data
US 2021/0079344 A1 Mar. 18, 2021

(30) Foreign Application Priority Data

Sep. 13, 2019 (EP) ..................................... 19197392

(51) Int. Cl.
| | |
|---|---|
| *C12N 5/0793* | (2010.01) |
| *C12N 5/079* | (2010.01) |
| *G01N 33/569* | (2006.01) |
| *A61K 35/30* | (2015.01) |

(52) U.S. Cl.
CPC ............ *C12N 5/0618* (2013.01); *A61K 35/30* (2013.01); *G01N 33/56966* (2013.01); *C12N 2501/998* (2013.01); *C12N 2506/45* (2013.01)

(58) Field of Classification Search
CPC ............ C12N 5/0618; C12N 2501/998; C12N 2506/45; A61K 35/30; G01N 33/56966
See application file for complete search history.

(56) References Cited

U.S. PATENT DOCUMENTS

| 8,252,585 B2 | 8/2012 | Carpenter |
| 9,803,174 B2 | 10/2017 | Carpenter |
| 10,072,245 B2 | 9/2018 | Bosio et al. |
| 2021/0079344 A1 | 3/2021 | Bosio et al. |

FOREIGN PATENT DOCUMENTS

WO 2021042027 A1 3/2021

OTHER PUBLICATIONS

Chinta et al. The International Journal of Biochemistry & Cell Biology 37, 942-946 (Year: 2005).*
Maria et al.; International Society for Neurochemistry, J. Neurochem. 139 (Suppl. 1), 8-26 (Year: 2016).*
Bantubungi et al. Mol. Cell. Neurosci. 37, pp. 454-470 (Year: 2008).*
Kirkeby et al., Cell Stem Cell 20, 135-148 (Year: 2017).*
CD117 MicroBead Kit, Human, Miltenyi Biotec B.V. & Co. KG, pp. 1-4.
Doi et al., Isolation of Human Induced Pluripotent Stem Cell-Derived Dopaminergic Progenitors by Cell Sorting for Successful Transplantation, Stem Cell Reports, vol. 2, No. 3, Mar. 11, 2014, pp. 337-350.
Kirkeby et al., Generation of Regionally Specified Neural Progenitors and Functional Neurons from Human Embryonic Stem Cells Under Defined Conditions, Cell Reports, vol. 1, No. 6, Jun. 28, 2012, pp. 703-714.
Kriks et al., Dopamine Neurons Derived from Human ES Cells Efficiently Engraft in Animal Models of Parkinson's Disease, Nature, vol. 480, No. 7378, Nov. 6, 2011, pp. 547-551.
Lehnen et al., IAP-Based Cell Sorting Results in Homogeneous Transplantable Dopaminergic Precursor Cells Derived from Human Pluripotent Stem Cells, Stem Cell Reports, vol. 9, Oct. 10, 2017, pp. 1207-1220.
Lehnen et al., IAP-Based Cell Sorting Results in Homogeneous Transplantable Dopaminergic Precursor Cells Derived from Human Pluripotent Stem Cells/Supplemental Information, Stem Cell Reports, vol. 9, Oct. 10, 2017, 26 pages.
Nolbrant et al., Generation of High-Purity Human Ventral Midbrain Dopaminergic Progenitors for in vitro Maturation and Intracerebral Transplantation, Nature Protocols, vol. 12, No. 9, Sep. 2017, pp. 1962-1979.

\* cited by examiner

*Primary Examiner* — Arthur S Leonard
*Assistant Examiner* — Masudur Rahman
(74) *Attorney, Agent, or Firm* — Kilpatrick Townsend & Stockton LLP (57) ABSTRACT

The present invention discloses an in vitro method for the generation of a cell composition comprising or consisting of ventral midbrain dopaminergic progenitor cells from a cell composition comprising pluripotent and/or multipotent stem cells, the method comprising the steps of A) differentiating said pluripotent and/or multipotent stem cells into ventral dopaminergic progenitor cells, thereby generating a cell composition comprising ventral dopaminergic progenitor cells comprising ventral midbrain dopaminergic progenitor cells and ventral hindbrain dopaminergic progenitor cells, and B) Enriching CD117 positive cells from said cell composition comprising ventral dopaminergic progenitor cells by using an antigen binding molecule specific for the CD117 antigen, thereby generating said cell composition comprising or consisting of ventral midbrain dopaminergic progenitor cells. Cell compositions obtainable by said method are also disclosed.

24 Claims, 7 Drawing Sheets
(5 of 7 Drawing Sheet(s) Filed in Color)

| | |
|---|---|
| lane 1 | MeanIntensity_CD117 |
| | MeanIntensity_CD304 |
| | MeanIntensity_K167 |
| | MeanIntensity_CD49d |
| | MeanIntensity_CD54 |
| | MeanIntensity_CD171 |
| | MeanIntensity_CD13 |
| | MeanIntensity_CD56 |
| | MeanIntensity_CD24 |
| | MeanIntensity_CD184 |
| | MeanIntensity_CD107a |
| | MeanIntensity_SUSD2 |
| | MeanIntensity_CD49f |
| | MeanIntensity_CD106 |
| | MeanIntensity_CD298 |
| | MeanIntensity_CD29 |
| | MeanIntensity_CD51 |
| | MeanIntensity_CD47 |
| | MeanIntensity_CD233 |
| | MeanIntensity_CD239 |
| | MeanIntensity_CD55 |
| | MeanIntensity_LAMP5 |
| | MeanIntensity_CD146 |
| | MeanIntensity_CD36 |
| | MeanIntensity_LGR5 |
| | MeanIntensity_CD321 |
| | MeanIntensity_CD156c |
| | MeanIntensity_PTK7 |
| lane 29 | MeanIntensity_CD276 |

FIG. 6B

METHOD FOR THE GENERATION OF A CELL COMPOSITION VENTRAL MIDBRAIN PATTERNED DOPAMINERGIC PROGENITOR CELLS

CROSS-REFERENCES TO RELATED APPLICATIONS

This application claims priority to European Patent Application No. 19197392.4, filed on Sep. 13, 2019, the content which is incorporated by reference in its entirety.

FIELD OF THE INVENTION

The present invention relates to the field of generation of a composition comprising or consisting of ventral midbrain dopaminergic progenitor cells from a starting cell composition comprising pluripotent and/or multipotent stem cells. In particular, it relates to a method of the generation a composition comprising or consisting of ventral midbrain dopaminergic progenitor cells that is depleted of undesired cell populations such as ventral hindbrain dopaminergic progenitor cells from a starting cell composition comprising pluripotent and/or multipotent stem cells.

BACKGROUND OF THE INVENTION

Parkinson's Disease (PD) is one of the most common neurodegenerative diseases mainly affecting the motor system. PD is characterized by the selective loss of highly specialized dopaminergic (DA) neurons in the substantia nigra pars compacta (SNpc) (Moore et al., Annu Rev Neurosci., 2005; 28:57-87). The loss of these DA neurons leads to the pathophysiological symptoms such as resting tremor and bradykinesia which can be treated with specific drugs like L-DOPA. However, these drugs do not alter the progression of PD and are only effective in early stages of the disease.

Proof-of-concept studies using early fetal midbrain tissue as a source of DA neurons have shown long-term survival and efficacy increasing the life quality of PD patients and thus supporting the suitability of cell-based therapies of PD (Barker et al., Nat Rev Neurol., 2015 Sep. 11(9):492-503). However, the fetal brain tissue is difficult to standardize and its use is problematic in terms of ethics. The successful derivation of mesencephalic dopaminergic neurons out of PSC has been shown by many researches in different labs including ours. Resulting cells meet most of the criteria for future clinical application in PD patients. Comparison of their functionality with fetal mesDA cells showed equal performance and no significant difference in preclinical studies (Grealish et al., Cell Stem Cell., 2014 Nov. 6; 15(5):653-65).

Over years the differentiation protocols were continuously optimized to achieve mesDA cells with optimal protein expression profiles, defined cryopreservation and QC assays according to latest knowledge and publications. The research teams further advanced to GMP compliant manufacturing to enable clinical use on humans. The current state of the art protocol (Nolbrant et al., Nat Protoc., 2017 Sep. 12(9):1962-1979) generates high quality cells regarding the expression of desired markers such as FoxA2 and Lmx1A. However, the in vitro generated cells achieve diversified in vivo results with respect to number of TH+ cells within the graft, its size and the motoric improvement of transplanted animals (Kirkeby et al., Cell Stem Cell., 2017 Jan. 5; 20(1):135-148). Thus, there is still a lack of information that would allow to specifically highlight the best performing cell phenotype to cure PD. Especially, the ventral midbrain and ventral hindbrain dopaminergic progenitor cells show high similarity in their expression profiles, thus making it difficult to determine the fate of mid- and hindbrain dopaminergic progenitor cells with respect to terminally differentiated dopaminergic subpopulations.

BRIEF SUMMARY OF THE INVENTION

Surprisingly it was found that the surface marker CD117 (c-Kit) is highly expressed on ventral midbrain dopaminergic progenitor cells but not on ventral hindbrain dopaminergic progenitor cells when a cell composition comprising pluripotent and/or multipotent stem cells is differentiated into ventral dopaminergic progenitor cells. The ventral midbrain progenitor cells are to a certain extend also positive for CD171 (L1CAM).

The well-known differentiation protocols for differentiation of pluripotent and/or multipotent stem cells into ventral dopaminergic progenitor cells that have been developed so far result in a mixture of different cell types, comprising among others ventral midbrain dopaminergic progenitor cells and ventral hindbrain dopaminergic progenitor cells.

The identification of CD117 as a specific marker for ventral midbrain dopaminergic progenitor cells and/or CD171 as a specific marker for hindbrain midbrain dopaminergic progenitor cells allows for the separation and/or enrichment of these cells, especially the separation of these cells from often unwanted ventral hindbrain dopaminergic progenitor cells, since the dopaminergic neurons residing in the substantia nigra, which is the part mainly affected in Parkinson's Disease, originally arise from the ventral midbrain progenitor cells during the embryonic development.

The present invention discloses a method for separation, enrichment and/or isolation of ventral midbrain dopaminergic progenitor cells from a cell composition comprising pluripotent and/or multipotent stem cells. Also disclosed herein is a substantially pure composition of ventral midbrain dopaminergic progenitor cells obtainable by the method as disclosed herein.

Herein it is also disclosed that the method of the present invention can be performed in a closed system resulting in ventral midbrain dopaminergic progenitor cells generated under GMP or GMP-like conditions. Even more unexpectedly, it was found that the method of the present invention is accessible to an automated process using said closed system.

The cells of the composition obtained by the methods of the present invention may, for example, be used in cell replacement therapies for patients as a therapeutic treatment to ameliorate or reverse symptoms caused by the loss of dopaminergic neurons in a patient suffering from Parkinson's disease.

BRIEF DESCRIPTION OF THE DRAWINGS

The patent or application file contains several drawings executed in color. Copies of this patent or patent application publication with color drawings will be provided by the Office upon request and payment of the necessary fee.

FIG. 2: Both, the F5 iPS cells (A) as well as the ventral dopaminergic progenitor cells at d16 of differentiation (B)

were stained for the pluripotency marker Oct3/4 to detect pluripotent stem cells. In vitro differentiated cells lose their pluripotency during differentiation.

FIGS. 6A and 6B.

DETAILED DESCRIPTION OF THE INVENTION

In a first aspect the present invention provides an in vitro method for the generation of a cell composition comprising or consisting of ventral midbrain dopaminergic progenitor cells from a cell composition comprising pluripotent and/or multipotent stem cells, the method comprising the steps of
A) Differentiating said pluripotent and/or multipotent stem cells into ventral dopaminergic progenitor cells, thereby generating a cell composition comprising ventral dopaminergic progenitor cells comprising ventral midbrain dopaminergic progenitor cells and ventral hindbrain dopaminergic progenitor cells,
B) Enriching CD117 positive cells from said cell composition comprising ventral dopaminergic progenitor cells by using an antigen binding molecule specific for the CD117 antigen, thereby generating said cell composition comprising or consisting of ventral midbrain dopaminergic progenitor cells.

Said enrichment of CD117 positive cells from said cell composition comprising ventral dopaminergic progenitor cells by using an antigen binding molecule specific for the CD117 antigen may be a positive selection of CD117 positive cells from said composition that comprises CD117 positive cells and CD117 negative cells.

Methods and protocols for differentiating pluripotent and/or multipotent stem cells into ventral dopaminergic progenitor cells are well-known in the art and are disclosed for example Kirkeby et al., Cell Stem Cell., 2017 Jan. 5; 20(1):135-148, Nolbrant et al., Nat Protoc., 2017 Sep. 12(9):1962-1979.

Said method, wherein said method comprises additionally the step of depleting CD171 positive cells from said cell composition comprising ventral dopaminergic progenitor cells by using an antigen binding molecule specific for the antigen CD171.

Said method, wherein said method comprises the step of depleting CD171 positive cells from said cell composition comprising ventral dopaminergic progenitor cells before said enrichment of CD117 positive cells by using an antigen binding molecule specific for the antigen CD171, or depleting CD171 positive cells after said enrichment of CD117 positive cells by using an antigen binding molecule specific for the antigen CD171.

Said antigen binding molecule specific for the antigen CD171 may be an anti-CD171 antibody or antigen-binding fragment thereof.

The generated ventral dopaminergic progenitor cells may comprise ventral midbrain dopaminergic progenitor cells, ventral hindbrain dopaminergic progenitor cells, and other cells.

Said method may comprise the further step of dissociating the differentiated cells of step A) into a single cell suspension before enrichment of the CD117 and/or depletion of said CD171 positive cells.

Said method, wherein said pluripotent and/or multipotent stem cells may be proliferated in a proliferation step before step A).

Methods and protocols for proliferation of pluripotent and/or multipotent stem cells are well-known in the art and are disclosed for example in Lam et al., Biores Open Access., 2015 Apr. 1; 4(1):242-57.

Said method, wherein said method may be performed in a closed system.

Said method, wherein said method may be an automated method.

Said method, wherein said method may be an automated method in a closed system.

The surprisingly robust expression of antigen CD117 on the surface of the ventral midbrain dopaminergic progenitor cells may be exploited to establish an automated process in a closed system for enrichment of the ventral midbrain dopaminergic progenitor cells as disclosed herein.

Such a closed system allows to operate under GMP or GMP-like conditions ("sterile") resulting in cell compositions which are clinically applicable. Herein exemplarily the CliniMACS Prodigy® (Miltenyi Biotec GmbH, Germany) is used as a closed system. This system is disclosed in WO2009/072003. But it is not intended to limit the use of the method of the present invention to the CliniMACS® Prodigy.

The CliniMACS Prodigy® System is designed to automate and standardize complete cellular product manufacturing processes. It combines CliniMACS® Separation Technology (Miltenyi Biotec GmbH, Germany) with a wide range of sensor-controlled, cell processing capabilities.

Said method, wherein said antigen binding molecule specific for the CD117 antigen may be an anti-CD117 antibody or antigen-binding fragment thereof.

Said method, wherein the step of enrichment of said ventral midbrain dopaminergic progenitor cells may be performed by fluorescent activated cell sorting or magnetic cell sorting. If the enrichment step is performed by fluorescent activated cell sorting, said anti-CD117 antibody or antigen-binding fragment thereof may be coupled to a fluorophore. If the enrichment step is performed by magnetic cell sorting, said anti-CD117 antibody or antigen-binding fragment thereof may be coupled to a magnetic particle.

Said method, wherein said method may comprise additionally the step of depleting pluripotent and/or multipotent stem cells from said cell composition comprising or consisting of ventral midbrain dopaminergic progenitor cells by using an antigen binding molecule specific for a pluripotent stem cell surface marker.

Said method, wherein the step of depleting pluripotent and/or multipotent stem cells may be performed by fluorescent activated cell sorting or magnetic cell sorting.

Said antigen binding molecule specific for a pluripotent stem cell marker may be selected from the group consisting of SSEA4, UEA-1, SSEA-3, Tra-1-60, Tra-1-81, SSEA-5, CD90 and CD30.

Said antigen binding molecule specific for a pluripotent stem cell marker may be SSEA4.

Said method, wherein the ventral midbrain dopaminergic progenitor cells may be human or non-human primate cells.

In another aspect the present invention provides substantially pure composition of ventral midbrain dopaminergic progenitor cells obtainable by the method as disclosed herein.

In a further aspect the present invention provides a pharmaceutical composition comprising ventral midbrain dopaminergic progenitor cells obtainable by the method as disclosed herein and a pharmaceutical acceptable carrier.

In another aspect the present invention provides a composition of ventral midbrain dopaminergic progenitor cells obtainable by the method as disclosed herein for use in treatment of neurological disorders.

The treatment of neurological disorders may be a cell replacement therapy in a subject (a patient). Said replacement therapy may be a therapeutic treatment to ameliorate or reverse symptoms caused by the loss of dopaminergic neurons in subject (a patient) suffering for example from Parkinson's disease.

All definitions, characteristics and embodiments defined herein with regard to an aspect of the invention, e.g. the first aspect of the invention, also apply mutatis mutandis in the context of the other aspects of the invention as disclosed herein.

In addition to above described applications and embodiments of the invention further embodiments of the invention are described in the following without intention to be limited to these embodiments.

Embodiments

In a first embodiment of the present invention the method for the generation of a cell composition comprising or consisting of ventral midbrain dopaminergic progenitor cells from a cell composition comprising pluripotent and/or multipotent stem cells comprises the steps of:
  a) differentiating said pluripotent and/or multipotent stem cells into ventral dopaminergic progenitor cells, thereby generating a cell composition comprising ventral dopaminergic progenitor cells comprising ventral midbrain dopaminergic progenitor cells and ventral hindbrain dopaminergic progenitor cells by using standard and well-known differentiation protocols
  b) contacting the differentiated cells of step a) with an antigen-binding molecule specific for the CD117 antigen, wherein said antigen binding molecule is coupled to a tag, thereby labeling the CD117 positive cells,
  c) isolating the labeled CD117 positive cells, i.e. the ventral midbrain dopaminergic progenitor cells.

In one embodiment of present invention said method comprises a proliferation step of said pluripotent and/or multipotent stem cells before step a).

Often the amount of pluripotent and/or multipotent stem cells available is limited. A proliferation step can ensure that sufficient numbers of differentiated cells can be derived in order to achieve a therapeutic effective amount of cells for subsequent clinical application such as transplantation of these cells.

A proliferation step comprises culturing said pluripotent and/or multipotent stem cells in pluripotency conferring maintenance medium supporting undifferentiated expansion of pluripotent stem cells. Such media are well known to the person skilled in the art.

A differentiation step of said pluripotent stem and/or multipotent stem cells comprises adding differentiation inducing substances such as specialized cultivation media, cytokines, receptor antagonists or small molecules to the cultivation media. Also the cultivation matrix, i.e. the coating of the cell culture ware, may be used to bias the differentiation process by providing different proteins or chemical compounds that are in contact with the cells. Such substances are well known to the person skilled in the art.

The method may also comprise a dissociation step of the differentiated cells into a single cell suspension. Said dissociating step for dissociating the cells may be performed by mechanical means, enzymatic and/or chemical agents. Such processes for dissociating cells are well known to the person skilled in the art.

Steps b) ("contacting") and c) ("isolating") may be performed in combination using e.g. fluorescent-activated cell sorting using a flow sorter or magnetic cell sorting. Such processes for separating cells from other cells are well known in the art.

In one embodiment of the invention said method may be performed in a closed system.

Some or all steps a) to c) and optionally the proliferation step before step a) and optionally the dissociating step of differentiated cells may be performed in a closed system which allows to operate under GMP or GMP-like conditions resulting in compositions which are clinically applicable. The closed system may be any system which reduces the risk of cell culture contamination while performing culturing processes in a closed system under sterile conditions so that the cells subsequently are applicable to a patient.

In one embodiment of the invention said method may be an automated method (process).

The robust expression of CD117 on the surface of the ventral midbrain dopaminergic progenitor cells could surprisingly be exploited to establish an automated process in a closed system.

Such a closed system may be able to perform most, preferentially all steps mentioned above in an automated manner. Exemplarily the CliniMACS Prodigy® (Miltenyi Biotec GmbH, Germany) is used herein as a closed cell sample processing system on which an automated process may be implemented. This system is disclosed in WO2009/072003 in detail. But it is not intended to restrict the use of the method of the present invention to the CliniMACS Prodigy®.

In one embodiment of the invention in said method with steps a) to c) said tag is a fluorophore if step c) is performed by fluorescent-activated cell sorting using a flow sorter such as FACSAria™ (BD Biocsiences) or MoFlo™ XDP (Beckman Coulter) or MACSQuant® Tyto™ (Miltenyi Biotec GmbH), or said tag is a magnetic particle if step c) is performed using magnetic cell sorting such as MACS® (Miltenyi Biotec GmbH).

Definitions

Unless defined otherwise, technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

The term "pluripotent stem cell" as used herein refers to cells being capable to self-renew and have the potential to differentiate into any of the embryonic germ layers endoderm, mesoderm and ectoderm and cells derived from this. These criteria hold true for embryonic stem cells (ESC) and induced pluripotent stem cells (iPSC). Preferentially these cells are human. Human embryonic stem cells can be isolated from embryos without destruction as disclosed e.g. in WO 03/046141. Different degrees of pluripotency are known in the art, referred to as "primed state" pluripotent stem cells, "naive state" pluripotent stem cells or "reset stage" pluripotent stem cells.

The term "induced pluripotent stem cells (iPSC)" as used herein refers to pluripotent cells generated by conversion of cells of lower potency, i.e. more differentiated cells, typically a somatic cell, to a state of pluripotency, the resulting cells being capable to self-renew and having the potential to differentiate into any of the embryonic germ layers endoderm, mesoderm and ectoderm and cells derived from this. Reprogramming may be achieved by methods such as nuclear transfer, cell fusion, or factor induced reprogramming, i.e. induced expression of one or more reprogramming factors, such as but not limited to OCT4, SOX2, KLF4, C-MYC, NANOG, LIN28, etc. Reprogramming factors may be introduced as nucleic acids, or proteins by viral transduction or by transfection. Different culture conditions and reprogramming factor combinations may result in different degrees of pluripotency, referred to as "primed state" pluripotent stem cells, "naive state" pluripotent stem cells or "reset stage" pluripotent stem cells.

The term "multipotent stem cell" as used herein refers to progenitor cells that have the capacity to differentiate into multiple but limited cell types.

The term "cell composition comprising ventral dopaminergic progenitor cells" may comprise ventral midbrain dopaminergic progenitor cells, ventral hindbrain dopaminergic progenitor cells as well as dorsal midbrain dopaminergic progenitor cells which did not ventralized properly.

The term "cell composition comprising ventral midbrain dopaminergic progenitor cells" as used herein refers to a cell composition comprising at least 70%, at least 80%, at least 90%, at least 95%, at least 96%, at least 97%, at least 98%, or at least 99% ventral midbrain dopaminergic progenitor cells compared to all cells of said composition, whereby said ventral midbrain dopaminergic progenitor cells are positive cells for FoxA2, Otx2 and Nurr1, highly important intracellular marker for ventral midbrain patterned cells.

Cells may be derived in vitro from different starting cell compositions such as but not limited to embryonic stem cells, induced pluripotent stem cells, primary neural cells from embryonic or fetal midbrain or in vitro generated expandable neural stem cell lines or LT-NES®.

The term "differentiation" as used herein refers to cellular differentiation, a term used in developmental biology, and describes the process by which a less specialized cell becomes a more specialized cell type. In vitro, differentiation of stem cells can occur spontaneously or is induced intentionally by adding differentiation inducing substances such as specialized cultivation media, cytokines, receptor antagonists or small molecules to the cultivation media. Also the cultivation matrix, i.e. the coating of the cell culture ware, may be used to bias the differentiation process by providing different proteins or chemical compounds that are in contact with the cells.

The term "single cell suspension" as used herein refers to a cell suspension, wherein cells from a solid tissue or cell clusters from an in vitro cell culture have been separated from each other and maintained separated from each other. It is not contrary to the meaning of the term "single cell suspension" that a low percentage of cells may adhere to each other. Single cell suspension can be achieved by any mechanical, enzymatic or chemical means. Methods therefore are well known in the art and are partly disclosed herein. Important is that the single cell suspension achieved by such dissociating methods is capable for use in subsequent processes such as cell sorting.

The term "cell composition comprising pluripotent and/or multipotent stem cells" as used herein refers to a sample comprising pluripotent or multipotent stem cells and other cells in any ratio or a mixture of said pluripotent and/or multipotent stem cells to the other cells in that sample. Said other cells may be spontaneously differentiated cells originating from said pluripotent or multipotent stem cells. Said spontaneously differentiated cells are characterized by loss of expression of stem cell associated markers and initiation of expression of differentiation associated markers. Preferentially, the portion of said other cells within the starting cell compositions may not exceed 30%, 20%, 10%, 9%, 8%, 7%, 6%, 5%, 4%, 3%, 2%, 1% of all cells. Preferentially, the cells are viable. The cells may be originated from humans or animals, especially mammals including but not limited to mouse, rats, pigs, cattle, dog, monkey. Cells of tissue derived from adult brains, parts of adult brains, embryonic or fetal tissue can also be used. Furthermore, or in vitro generated expandable neural stem cell lines (NSCs) or LT-NES® may be used.

The term "marker" as used herein refers to a cell antigen that is specifically expressed by a certain cell type. Preferentially, the marker is a cell surface marker so that enrichment, isolation and/or detection of living cells can be performed. The markers may be positive selection markers such as CD117 as disclosed herein or may be negative selection markers such as SSEA4 as used herein. Cell antigens that are expressed intracellularly, e.g. structural or muscle proteins or transcription factors such as FoxA2 and Otx2 are analytical markers used to identify ventral midbrain dopaminergic progenitor cells such as, but cannot be used for enrichment of viable cells.

The term "expression" as used herein is defined as the transcription and/or translation of a particular nucleotide sequence driven by its promoter in a cell. The term "robust expression" as used herein refers to strong correlation of an antigen with a cellular phenotype (e.g. CD117 with FoxA2/Otx2 double positive ventral midbrain dopaminergic progenitor cells) and concomitant a sufficient strong expression of the same antigen allowing the implementation of an automated process for generation and separation of the cells expressing said antigen.

The term "generating" in the context of the generation of a cell composition comprising or consisting of ventral midbrain dopaminergic progenitor cells by the method of the present invention has the same meaning as the term "producing" or "manufacturing". These terms describe the fact that at least a part of the cells of a cell composition comprising pluripotent and/or multipotent stem cells are transformed to the target cells, i.e. ventral midbrain dopaminergic progenitor cells, which then are isolated from non-target cells such as ventral hindbrain dopaminergic progenitor cells as disclosed by the method of the present invention.

The term "tag" as used herein refers to the coupling of the antigen-binding molecule, e.g. an antibody or antigen-binding fragment thereof, to other molecules, e.g. particles, fluorophores, haptens like biotin, or larger surfaces such as culture dishes and microtiter plates. In some cases the coupling results in direct immobilization of the antigen-binding molecule, e.g. if the antigen-binding molecule is coupled to a larger surface of a culture dish. In other cases this coupling results in indirect immobilization, e.g. an antigen-binding molecule coupled directly or indirectly (via e.g. biotin) to a magnetic bead is immobilized if said bead is retained in a magnetic field. In further cases the coupling of the antigen-binding molecule to other molecules results not in a direct or indirect immobilization but allows for enrichment, separation, isolation, and detection of cells according to the present invention, e.g. if the antigen-binding molecule is coupled to a fluorophore which then allows discrimination of stronger labeled cells, weaker labeled cells, and non-labeled cells, e.g. via flow cytometry methods, like Flow sorting, or fluorescence microscopy.

The term "particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a lyophilised state prior to use in the present invention. The lyophilized particle is then reconstituted in convenient buffer before contacting the sample to be processed regarding the present invention.

The term "magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The term "antigen-binding molecule" as used herein refers to any molecule that binds preferably to or is specific for the desired target molecule of the cell, i.e. the antigen. The term "antigen-binding molecule" comprises e.g. an antibody or antigen-binding fragment thereof. The term "antibody" as used herein refers to polyclonal or monoclonal antibodies, which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies).

The term "antibody" comprises both intact molecules and antigen-binding fragments thereof, such as Fab, Fab', F(ab')2, Fv and single-chain antibodies. The linkage (coupling) between an antibody or antigen binding fragment thereof and a tag or particle can be covalent or non-covalent. A covalent linkage can be, e.g. the linkage to carboxyl-groups on polystyrene beads, or to NH2 or SH2 groups on modified beads. A non-covalent linkage is e.g. via biotin-avidin or a fluorophore-coupled-particle linked to anti-fluorophore antibody. Methods for coupling antibodies to particles, fluorophores, haptens like biotin or larger surfaces such as culture dishes are well known to the skilled person in the art.

The terms "specifically binds to" or "specific for" with respect to an antigen-binding molecule, e.g. an antibody or antigen-binding fragment thereof, refer to an antigen-binding molecule which recognizes and binds to a specific antigen in a sample, e.g. in the present invention to CD117, but does not substantially recognize or bind other antigens in said sample. An antigen-binding domain of an antibody or antigen binding fragment thereof that binds specifically to an antigen from one species may bind also to that antigen from another species. This cross-species reactivity is not contrary to the definition of "specific for" as used herein. An antigen-binding domain of an antibody or antigen binding fragment thereof that specifically binds to an antigen, e.g. the CD117 antigen, may also bind substantially to different variants of said antigen (allelic variants, splice variants, isoforms etc.). This cross reactivity is not contrary to the definition of that antigen-binding domain as specific for the antigen, e.g. for CD117.

As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The cluster of differentiation (CD) is a protocol used for the identification and investigation of cell surface molecules providing targets for immunophenotyping of cells. In terms of physiology, CD molecules can act in numerous ways, often acting as receptors or ligands important to the cell. CD117 (also termed c-KIT or SCFR) is a cytokine receptor expressed on the surface of hematopoietic stem cells as well as other cell types. CD117 is a receptor tyrosine kinase type III, which binds to stem cell factor, also known as "steel factor" or "c-kit ligand". When this receptor binds to stem cell factor (SCF) it forms a dimer that activates its intrinsic tyrosine kinase activity, that in turn phosphorylates and activates signal transduction molecules that propagate the signal in the cell.

The term "CD117 positive cell" or "CD117$^+$ cell" means that the cell expresses the antigen CD117 on its cell surface.

For removal, enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells.

An especially potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies or antigen binding fragments thereof can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching, sorting and/or detecting ventral midbrain dopaminergic progenitor cells from a cell composition comprising pluripotent and/or multipotent stem cells according to the present invention monoclonal antibodies or antigen binding fragments thereof are used in conjunction with colloidal superparamagnetic microparticles having an organic coating by e.g. polysaccharides (Magnetic-activated cell sorting (MACS®) technology (Miltenyi Biotec, Bergisch Gladbach, Germany)). These particles (nanobeads or MicroBeads) can be either directly conjugated to monoclonal antibodies or used in combination with anti-immunoglobulin, avidin or anti-hapten-specific MicroBeads. The MACS® technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s). In case of a positive selection the cells expressing the antigen(s) of interest, which attached to the magnetic column, are washed out to a separate vessel, after removing the column from the magnetic field. In case of a negative selection the antibody used is directed against surface antigen(s), which are known to be present on cells that are not of interest. After application of the cells/magnetic nanoparticles solution onto the column the cells expressing these antigens bind to the column and the fraction that goes through is collected, as it contains the cells of interest. As these cells are non-labeled by an antibody coupled to nanoparticles, they are "untouched". The procedure can be performed using direct magnetic labeling or indirect magnetic labeling. For direct labeling the specific antibody or antigen binding fragment thereof is directly coupled to the magnetic particle. Indirect labeling is a convenient alternative when direct magnetic labeling is not possible or not desired. A primary antibody, a specific monoclonal or polyclonal antibody, a combination of primary antibodies, directed against any cell surface marker can be used for this labeling strategy. The primary antibody can either be unconjugated, biotinylated, or fluorophore-conjugated. The magnetic labeling is then achieved with anti-immunoglobulin MicroBeads, anti-biotin MicroBeads, or anti-fluorophore MicroBeads. The above-described processes can also be performed in a closed cell sample processing system such as CliniMACS® (Miltenyi Biotec GmbH, Germany) or CliniMACS® Prodigy (Miltenyi Biotec GmbH, Germany).

The term "substantially pure composition of ventral midbrain dopaminergic progenitor cells" as used herein refers to a cell composition comprising at least 70%, more preferentially at least 90%, most preferentially at least 95% of ventral midbrain dopaminergic progenitor cells in the cell composition obtained by the method of the present invention.

The ventral midbrain dopaminergic progenitor cells obtainable by the methods disclosed herein may be used for subsequent steps such as research, diagnostics, pharmacological or clinical applications known to the person skilled in the art. Purification of ventral midbrain dopaminergic progenitor cells from the variety of other cell types in the original tissue (e.g. adult brain, fetal cells) as well as in pluripotent stem cell differentiation cultures is a prerequisite for molecular, biochemical or electrophysiological in vitro analysis.

The enriched ventral midbrain dopaminergic progenitor cells can also be used as a pharmaceutical composition in the therapy, e.g. cellular therapy, or prevention of diseases. The pharmaceutical composition may be transplanted into an animal or human, preferentially a human patient. The pharmaceutical composition can be used for the treatment and/or prevention of diseases in mammals, especially humans, possibly including administration of a pharmaceutically effective amount of the pharmaceutical composition to the mammal. The disease may be any disease, which can be treated and/or prevented through the presence of ventral midbrain dopaminergic progenitor cells and/or through increasing the concentration of the relevant cells in/at the relevant place, e.g. in the place of the lost tissue of a patient suffering from Parkinson's disease. The treated and/or preventively treated disease may be any disease, which displays symptoms caused by the loss of dopaminergic neurons in a patient. The treatment may be the transplantation of enriched ventral midbrain dopaminergic progenitor cells to the relevant place of the brain of the patient. Pharmaceutical compositions of the present disclosure may be administered in a manner appropriate to the disease to be treated or prevented. The quantity and frequency of administration will be determined by such factors as the condition of the patient, and the type and severity of the patient's disease, although appropriate dosages may be determined by clinical trials.

The composition of ventral midbrain dopaminergic progenitor cells obtained by the method of the present invention may be administered either alone, or as a pharmaceutical composition in combination with diluents and/or with other components such as cytokines or cell populations. Briefly, pharmaceutical compositions of the present invention may comprise the ventral midbrain dopaminergic progenitor cells of the present invention as described herein, in combination with one or more pharmaceutically or physiologically acceptable carriers, diluents or excipients. Such pharmaceutically or physiologically acceptable carriers may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Neurodegenerative diseases occur as a result of neurodegenerative processes in a subject.

Neurodegeneration is the progressive loss of structure or function of neurons, including death of neurons. Parkinson's Disease (PD) is one of the most common neurodegenerative diseases mainly affecting the motor system. PD is characterized by the selective loss of highly specialized dopaminergic (DA) neurons in the substantia nigra pars compacta (SNpc). The loss of these DA neurons leads to the pathophysiological symptoms such as resting tremor and bradykinesia which can be treated with specific drugs like L-DOPA. However, these drugs do not alter the progression of PD and are only effective in early stages of the disease.

The term "closed system" as used herein refers to any closed system which reduces the risk of cell culture contamination while performing culturing processes such as the introduction of new material and performing cell culturing steps such as proliferation, differentiation, activation, and/or separation of cells. Such a system allows to operate under GMP or GMP-like conditions ("sterile") resulting in cell compositions which are clinically applicable. Herein exemplarily the CliniMACS Prodigy® (Miltenyi Biotec GmbH, Germany) is used as a closed cell sample processing system. This system is disclosed in WO2009/072003. But it is not intended to restrict the use of the method of the present invention to the CliniMACS® Prodigy.

The terms "automated method" or "automated process" as used herein refer to any process being automated through the use of devices and/or computers and computer software which otherwise would or could be performed manually by an operator. Methods (processes) that have been automated require less human intervention and less human time to deliver. In some instances the method of the present invention is automated when at least one step of the present method is performed without any human support or intervention. Preferentially the method of the present invention is automated when all steps of the method as disclosed herein are performed without human support or intervention. Preferentially the automated process is implemented on a closed system such as CliniMACS® Prodigy as disclosed herein.

The term "therapeutic effective amount" means an amount which provides a therapeutic benefit in a patient.

As used herein, the term "subject" refer to an animal. Preferentially, the subject is a mammal such as mouse, rat, cow, pig, goat, chicken dog, monkey or human. More preferentially, the individual is a human.

This invention is further illustrated by the following examples, which are not to be construed in any way as imposing limitations upon the scope thereof.

EXAMPLES

Example 1

Proliferation of Pluripotent and/or Multipotent Stem Cells

When the cells have reached about 90% confluency the cells were splitted. For that the medium was removed and the cells were washed with PBS and then harvested with TrypLE (Life Technologies, 12563029). The cell suspension was centrifuged for 5 min at 300×g. The supernatant was removed and diluted in fresh StemMACS iPS-Brew XF medium (Miltenyi Biotec, 130-104-368). After determining the cell number 80.000-100.000 cells per 6-well were seeded in 2 ml fresh iPS Brew medium with Thiazovivin (2 µM; Miltenyi Biotec 130-104-461) in 6-well plates which were coated with Laminin-521 (0.5 µg/cm$^2$; BioLamina LN521-02) diluted in PBS$^{++}$ over night at 4° C. After two days the medium was changed on daily basis without Thiazovivin until reaching about 90% confluency.

Example 2

Differentiation of Pluripotent and/or Multipotent Stem Cells into Ventral Dopaminergic Progenitor Cells For differentiation the human iPS cells were harvested with TrypLE (Life Technologies, 12563029). Single cells were seeded in plates coated with Laminin-111 (1 µg/cm$^2$; BioLamina LN111-02) at a concentration of 2.25·10^5 cells per 6-well in DMEM-F12:MACS Neuro medium (1:1; Thermo Fisher Scientific, 11320033; Miltenyi Biotec, 130-093-570), supplemented with N2 supplement (1:100; Thermo Fisher Scientific, 17502048), NeuroBrew-21 w/o vitamin A (1:50; Miltenyi Biotec 130-097-263) and L-Glutamin (2 mM; Lonza, 17-605E). Additionally, the ROCK-Inhibitor Thiazovivin (2 Miltenyi Biotec, 130-104-461) was added for the first two days.

From d0 to d9 the following differentiation and patterning factors were freshly added to the differentiation medium on the day of medium change: SB431542 (10 µM; Miltenyi Biotec, 130-106-543), Noggin (100 ng/ml; Miltenyi Biotec, 130-103-456), CHIR99021 (0.7 µM; Miltenyi Biotec, 130-106-539), hSHH-C24-II (600 ng/ml; Miltenyi Biotec, 130-095-730). From d2 to d9 Purmorphamine (0.5 µM; Miltenyi Biotec, 130-104-465) was added to the medium. The medium was changed on d2, d4, d7 and d9. Between d4 and d10 the concentrations of N2 supplement and NeuroBrew-21 w/o vitamin A was halved accordingly. On d9 the differentiation and patterning factors were removed and only FGF-8b (100 ng/ml; Miltenyi Biotec, 130-095-740) was added to the differentiation medium.

On day 11 of differentiation the cells were dissociated into single cells with TrypLE and either used for an experiment for quality control or replated on Laminin-111 coated plates (800.000 cells per cm$^2$) in MACS Neuro medium supplemented with NeuroBrew-21 w/o vitamin A (1:50), L-Glutamin (2 mM), FGF-8b (100 ng/ml), ascorbic acid (200 µM; Sigma-Aldrich, A5960) and BDNF (20 ng/ml; Miltenyi Biotec, 130-096-286). Additionally, Thiazovivin (2 µM) was added for the first three days (d11-d14). The medium was changed on d14.

On day 16 of differentiation the cells were dissociated into single cells with TrypLe and either used for an experiment for quality control or were frozen in Cryo-Brew (Miltenyi Biotec, 130-109-558) for further use.

Example 3

Verification of CD117 as a Marker for Ventral Midbrain Dopaminergic Progenitor Cells Derived from Different Pluripotent Stem Cell Sources To verify that the correlation of CD117 with the highly important intracellular marker FoxA2, thus highlighting the ventral midbrain dopaminergic progenitor cells, is independent from the sources auf pluripotent stem cells. We could show this correlation for one iPS line (F5) and one ES line (1(15).

Example 4

Sorting Strategy of CD117 Positive Cells

Figure 1:
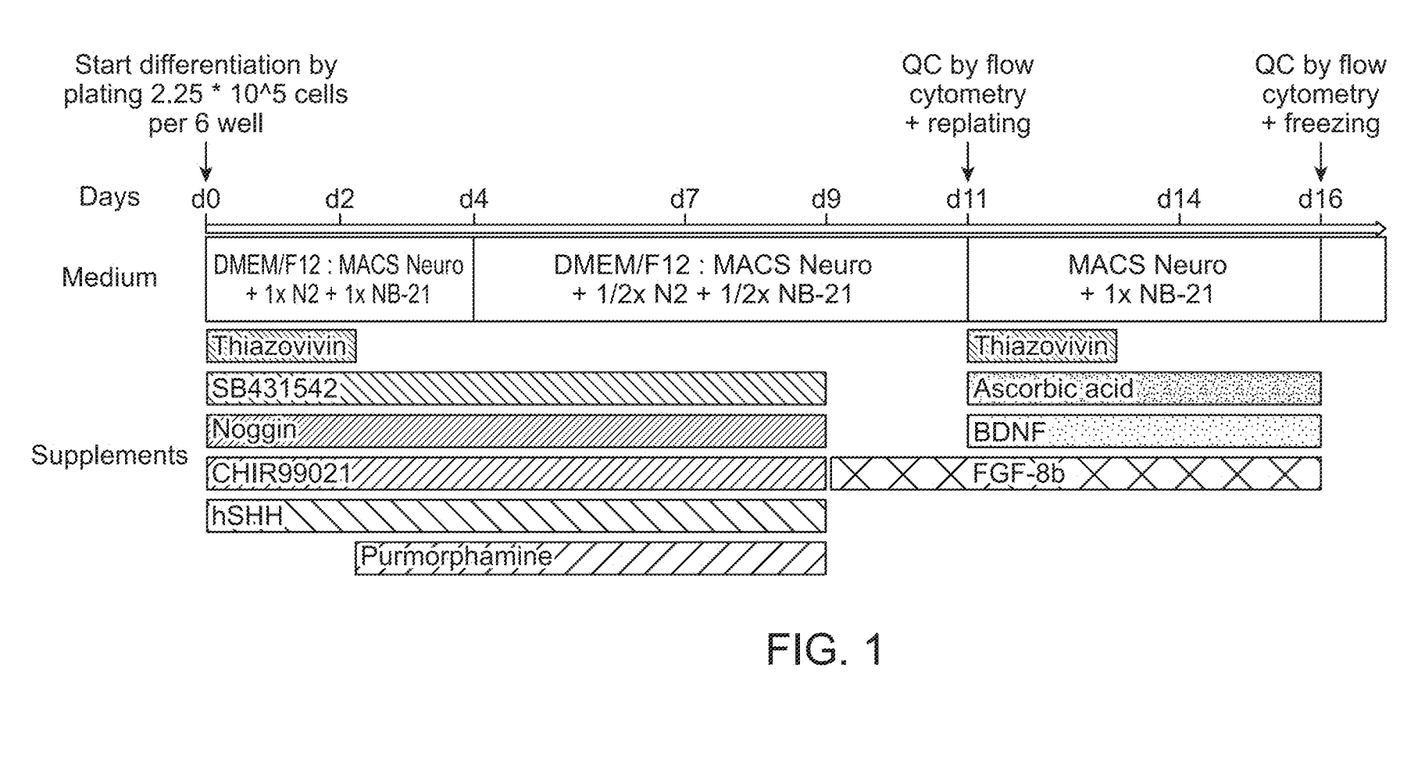
FIG. 1: Schematic illustration of the differentiation protocol for in vitro generation of ventral dopaminergic progenitor cells showing the used media as well as the patterning factors and small molecules.
Figure 2:
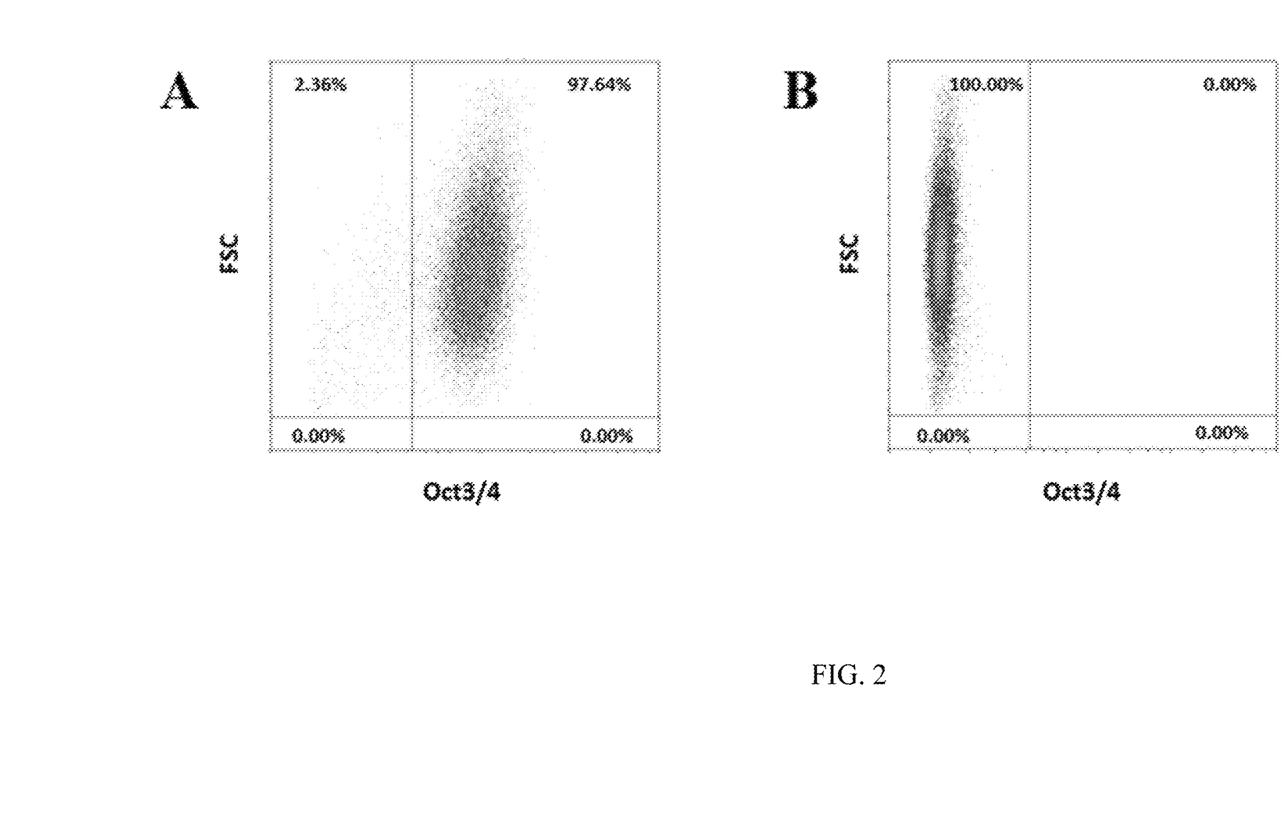
Figure 3:
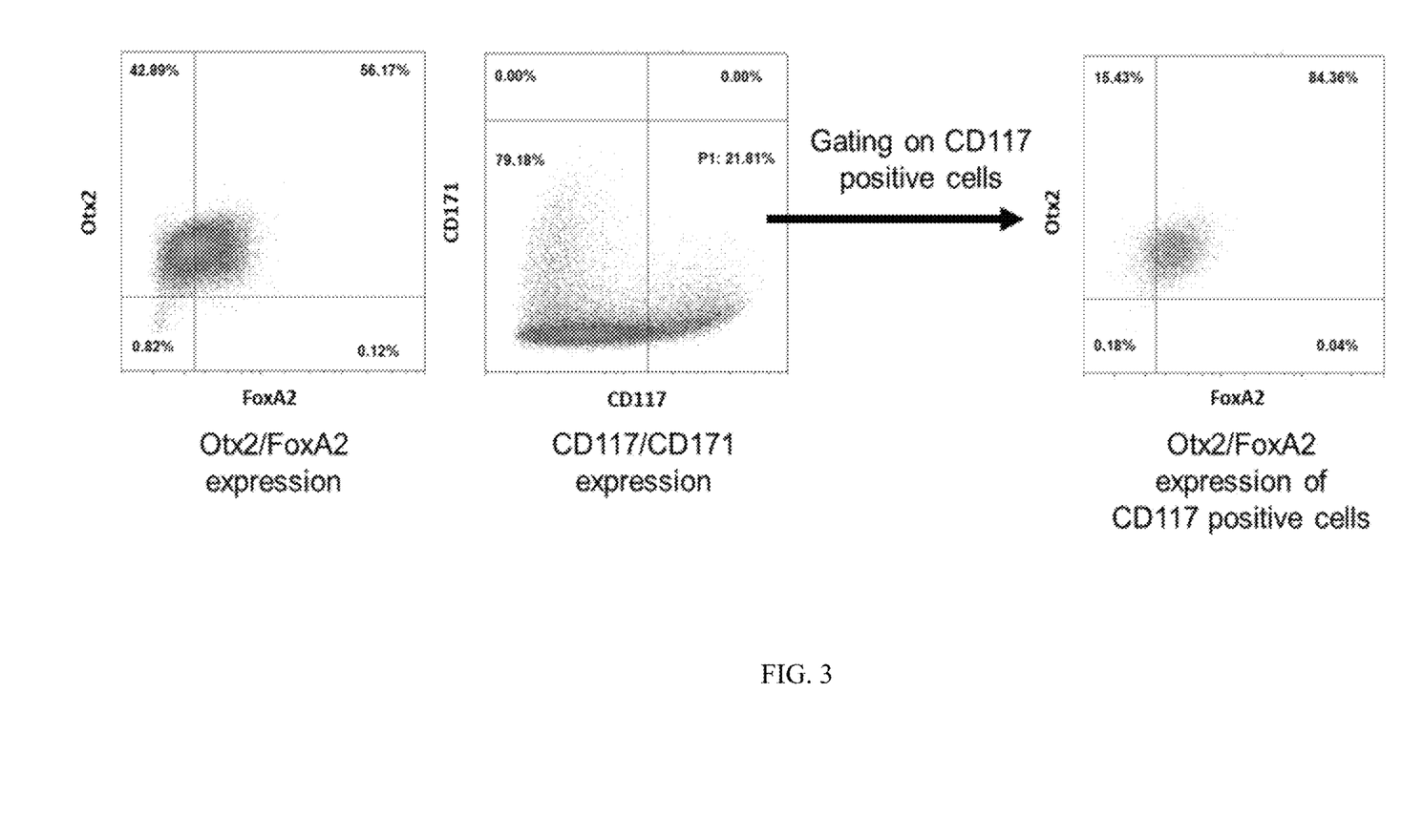
FIG. 3: Sorting strategy using CD117 as an enrichment marker so enrich Otx2/FoxA2 double positive cells. The gating for CD117 positive cells results in an increase of Otx2/FoxA2 double positive cells from 56% to 83%.
Figure 4:
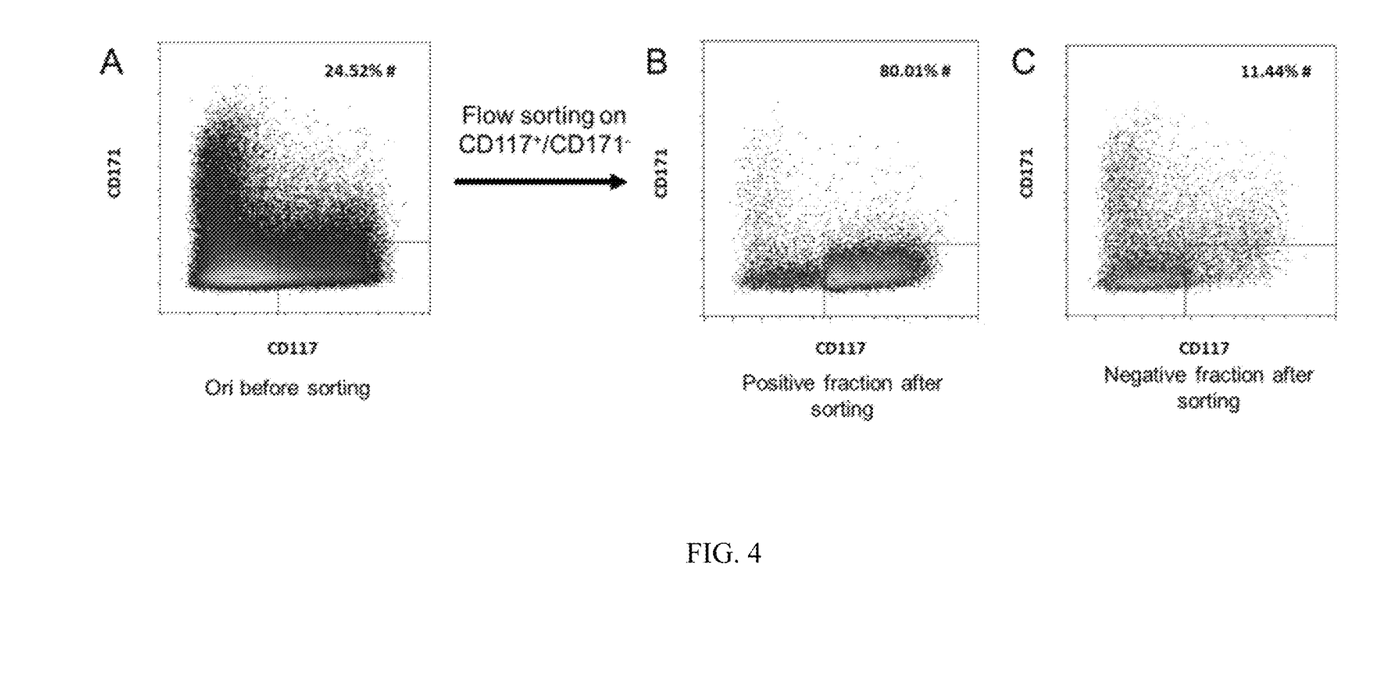
FIG. 4: On d16 of differentiation the ventral dopaminergic progenitor cells underwent a Flow sorting using an anti-CD117 antibody as an enrichment marker and an anti-CD171 antibody as a depletion marker. The target population is shown in (A) whereas (B) shows the positive fraction and (C) shows the negative fraction after sorting. Flow sorting enriched the desired CD117 positive cells with a purity of 80%.
Figure 5:
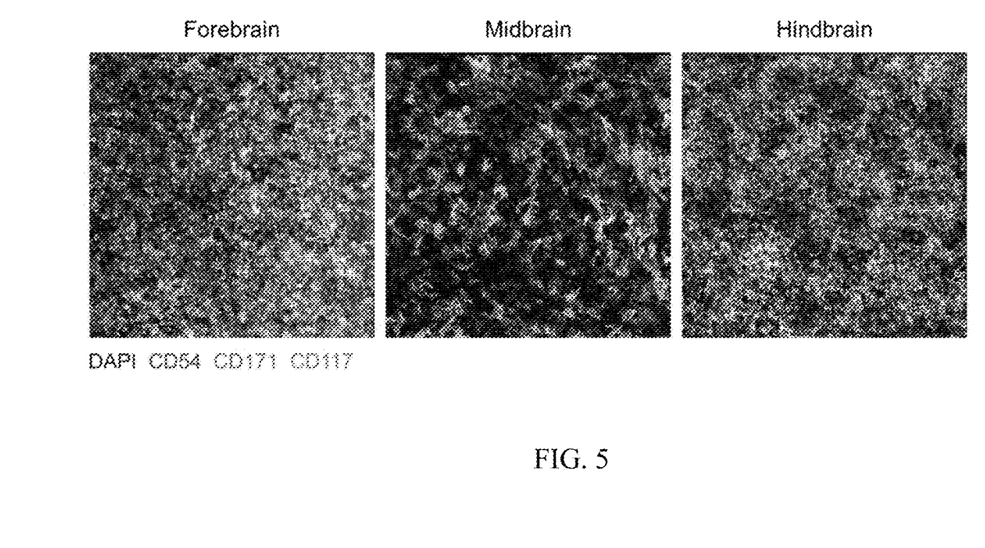
FIG. 5: Overlay of multidimensional staining of fore-, mid- and hindbrain in vitro differentiated cells. The in vitro differentiated cells towards fore-, mid- and hindbrain were stained with antibodies against more than 100 extra- and intracellular targets to detect preferably surface markers that enable the precise discrimination between these 3 cells types.
Figure 6A:
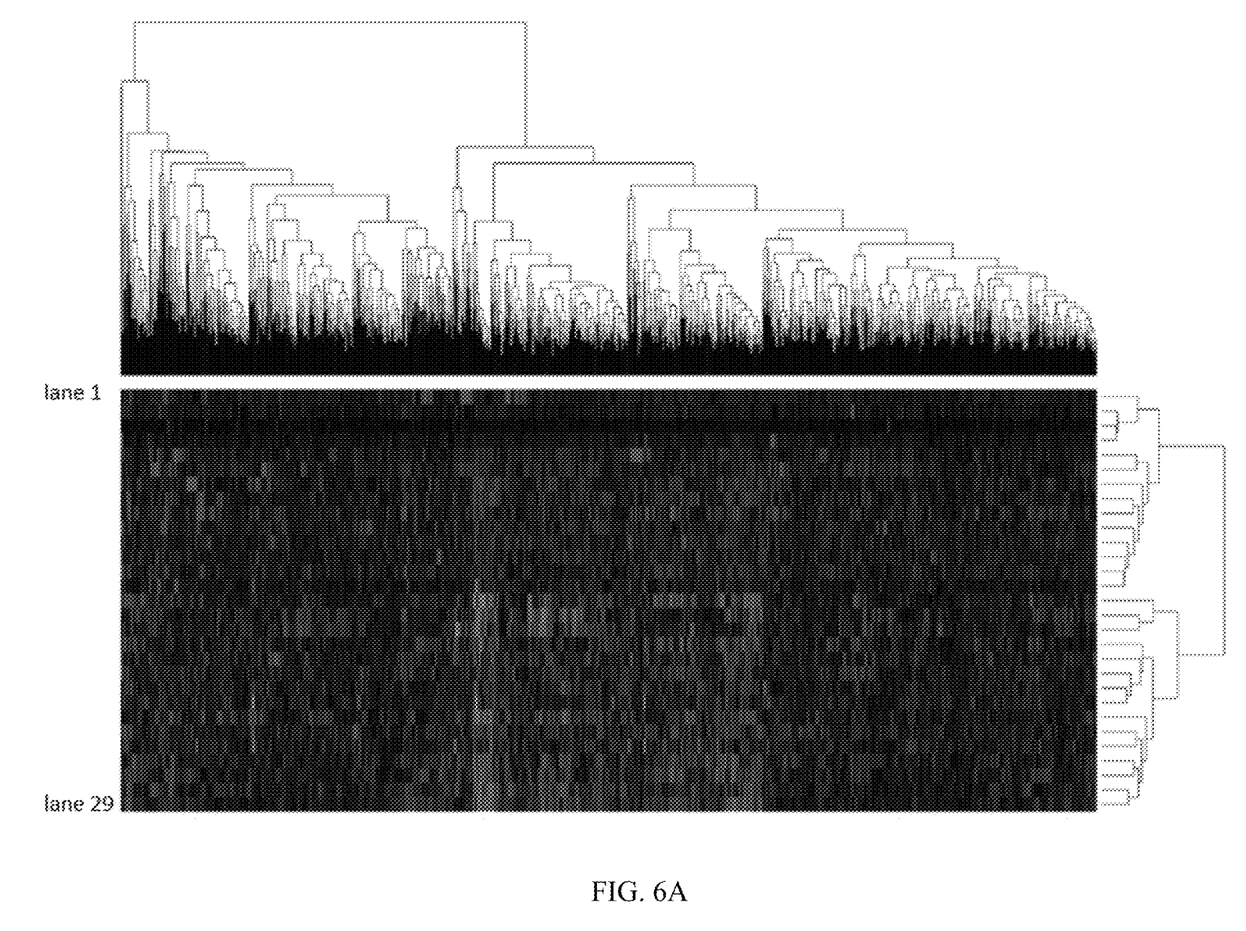
FIG. 6A: Best candidates of the multidimensional staining of were plotted to detect similarities and cell clusters sharing the same expression patterns. Beside others, CD117 was discovered to be highly expressed on ventral midbrain dopaminergic progenitor cells and CD171 to be highly expressed on ventral hindbrain dopaminergic progenitor cells.
Figure 6B:
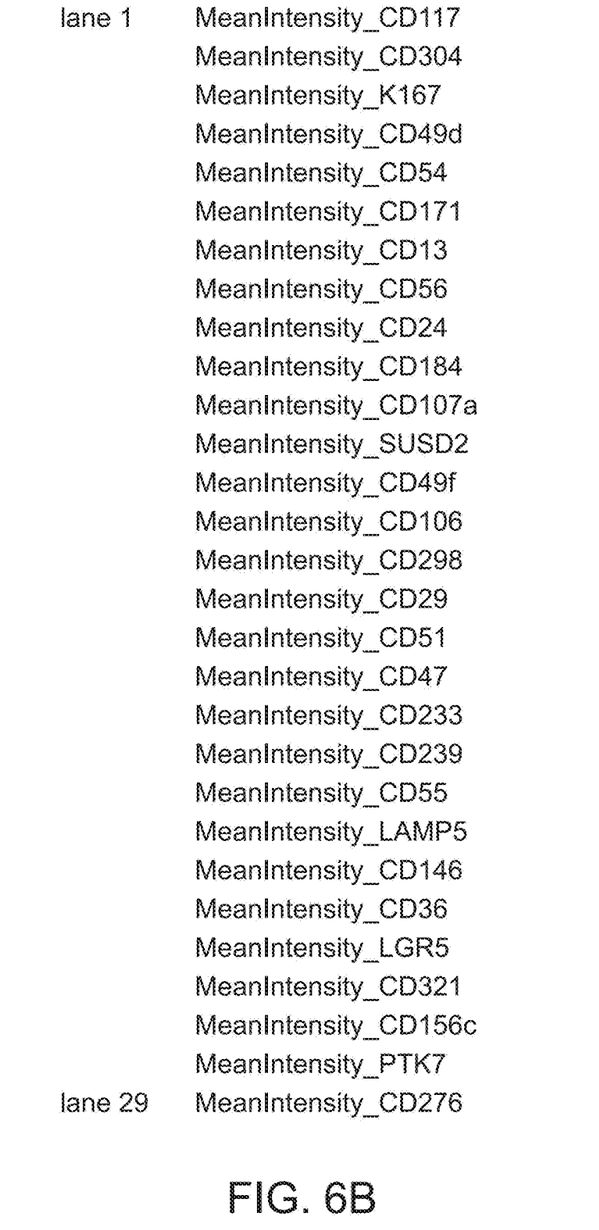
FIG. 6B: Labeling of the clustered proteins from line 1 to line 29 as given in FIG. 6A are shown.

The cell sorting of CD117 positive cell can be performed either by magnetic sorting using Microbeads or Flow sorting using MACSQuant® Tyto™ (Miltenyi Biotec). In case of Flow sorting the cells the cells were harvested with TrypLE on day 16 of differentiation and up to 10^7 single cells were stained in 100 µl medium supplemented with 2 µM Thiazovivin. The anti-CD117 antibody was diluted 1:11 and stained for 10 min at 4° C. After the staining the cells were washed with 1 ml medium per 100 µl cell suspension and centrifuged for 5 min at 300×g. The supernatant was removed and the cells were resuspended in an appropriate volume of medium before the cell sorting for CD117 positive cells by MACSQuant® Tyto™ (Miltenyi Biotec). This type of cell sorting can increase the percentage of Otx2/FoxA2 double positive cells to over 80% compared to 56% before cell sorting (FIG. 3). Additionally, the cells can be further stained with anti-CD171 antibody simultaneously to stain the undesired CD171 positive cells.

In case of magnetic cell sorting using Microbeads (Miltenyi Biotec) one can use the CD117 Microbead Kit (Miltenyi Biotec, 130-091-332) according to the data sheet to enrich CD117 positive cells.

Example 5

Automated Differentiation and Isolation of Ventral Midbrain Dopaminergic Progenitor Cells Using the CliniMACS Prodigy® System The automation of the differentiation and isolation of ventral midbrain dopaminergic progenitor cells based on CD117 expression was implemented as follows. All cultivation steps were performed in the CliniMACS Prodigy tubing set TS730, modified by connecting tube extensions, accessories containing cell sampling pouches as well as Advanced cell culture bag (ACCB, Miltenyi Biotec, prototypes). First, a highly gas permeable ACCB containing 5 layers of polystyrol cultivation surface (total 500 cm$^2$) was sterilely connected to the tube behind valve 22 using a 1 meter tube extension (Miltenyi Biotec, 130-017-904).

After priming of the tubing step, i.e. conditioning, using rinsing buffer, a Laminin-521 diluted in PBS$^{++}$ (0.5 µg/cm$^2$; BioLamina LN521-02) was transferred into said ACCB and incubated over night at 4° C. After coating, the Laminin-521 solution was removed and 7.5×10$^6$ iPS cells were suspended in 75 ml StemMACS™ iPS-Brew XF Media (Miltenyi Biotec), supplemented with 2 µM Thiazovivin, and sterilely transferred into a Cell transfer bag, divided by a bag clamp and another 75 ml StemMACS™ iPS-Brew XF Media (Miltenyi Biotec) supplemented with 2 µM Thiazovivin was filled into the bag above the bag clamp. The bag was sterilely connected to TS730 and the cell suspension was transferred into the ACCB. After that, the bag clamp was opened to flush out and transfer remaining cells out of the cell transfer bag into the connected ACCB behind valve 22. The ACCB was placed into an adjacent gas and heat controlled cell culture incubator (CentriCult Unit=CCU). Automated media exchange was conducted at day 2 (full media change) and day 3-5 (70% media exchange using) using StemMACS™ iPS-Brew XF Media without addition of Thiazovivin. At day 4 of iPSC expansion, the CCU was coated with Laminin-111 diluted in PBS$^{++}$ (1 µg/cm$^2$; BioLamina LN111-02) for differentiation and incubated over night at 4° C. At day 5 of iPS culture, iPSC were harvested form the ACCB, by first washing with media, incubation with TrypLE (Life Technologies, 12563029) for 7 min, followed by enzyme inhibition using 0.5 mg/ml soybean inhibitor (Soybean Trypsin-Inhibitor; Life Technologies, 17075029) in PBS. Cells were transferred into the CCU, a sample was transferred into a sampling pouch as part of a connected accessory tube (Triple Sampling Adapter, Miltenyi Biotec 130-017-907) behind valve 20 (connected using a three-way stop cock behind valve 20) to assess cell concentration. 120×10$^6$ cells were harvested and washed 3 times, i.e. sedimented by horizontal centrifugation and resuspended in media, using the centrifugation unit (CCU) and resuspended in 120 ml (1×10$^6$/ml) differentiation media. 20 ml of cell suspension was discarded (pumped into bag 5) to adjust to 100 ml of suspension culture volume within the CCU. The CCU was incubated at 37° C. headspace gas was adjusted to 5% CO$_2$. As differentiation media DMEM-F12:MACS Neuro medium (1:1; Thermo Fisher Scientific, 11320033; Miltenyi Biotec, 130-093-570), supplemented with N2 supplement (1:100; Thermo Fisher Scientific, 17502048), NeuroBrew-21 w/o vitamin A (1:50; Miltenyi Biotec 130-097-263) and L-Glutamin (2 mM; Lonza, 17-605E). Additionally, the ROCK-Inhibitor Thiazovivin (2 µM; Miltenyi Biotec, 130-104-461) was added for the first two days. From d0 to d9 the following differentiation and patterning factors were freshly added to the differentiation medium on the day of medium change: SB431542 (10 µM; Miltenyi Biotec, 130-106-543), Noggin (100 ng/ml; Miltenyi Biotec, 130-103-456), CHIR99021 (0.7 µM; Miltenyi Biotec, 130-106-539), hSHH-C24-II (600 ng/ml; Miltenyi Biotec, 130-095-730). From d2 to d9 Purmorphamine (0.5 µM; Miltenyi Biotec, 130-104-465) was added to the medium. Between d4 and d10 the concentrations of N2 supplement and NeuroBrew-21 w/o vitamin A was halved accordingly. On d9 the differentiation and patterning factors were removed and only FGF-8b (100 ng/ml; Miltenyi Biotec, 130-095-740) was added to the differentiation medium. Media changes were conducted at days 2, 4, 7 and 9, the differentiation media supplemented according to the above instructions for the respective day of differentiation. On day 10 a new ACCB (surface area 200 cm$^2$) was welded to the tube behind valve 22 replacing the initial culture bag for the iPS expansion step, and was coated with Laminin-111 over night at 4° C. (as before). On day 11 of differentiation, the cells were dissociated into single cells with TrypLE (Life Technologies) and optionally passed through a tubing loop equipped with cell strainer units with decreasing pore size, in this case 100, 100, 70, 30 µm), integrated between the CCU and valve 24 using 2 three-way stop cocks, thereby breaking down cell aggregates and or remove unwanted cell clusters. Cells were transferred into the CCU, a sample was transferred into a sampling pouch as part of a connected accessory tube behind valve 20 (connected using a three-way stop cock behind valve 20) to assess cell concentration. The cells were harvested and washed 3 times, i.e. sedimented by horizontal centrifugation and resuspended in media, using the centrifugation unit (CCU) and resuspended in 100 ml (800.000 cells per cm$^2$) differentiation media, i.e. MACS Neuro medium supplemented with NeuroBrew-21 w/o vitamin A (1:50), L-Glutamin (2 mM), FGF-8b (100 ng/ml), ascorbic acid (200 µM; Sigma-Aldrich, A5960) and BDNF (20 ng/ml; Miltenyi Biotec, 130-096-286). Additionally, Thiazovivin (2 µM) was added for the first three days (d11-d14). The medium was changed on d14. On day 16 of differentiation, the cells were dissociated into single cells with TrypLE (Life Technologies) and optionally passed through a tubing loop equipped with cell strainer units with decreasing pore size (in this case 100, 100, 70, 30 µm), integrated between the CCU and valve 24 using 2 three-way stop cocks, thereby breaking down cell aggregates and or remove unwanted cell clusters. Cells were transferred into the CCU, a sample was transferred into a sampling pouch as part of a connected accessory tube behind valve 20 (connected using a three-way stop cock behind valve 20) to assess cell concentration. 225×10$^6$ cells were harvested and washed 3 times, i.e. sedimented by horizontal centrifugation and resuspended in media, using the centrifugation unit (CCU) and resuspended in 10 ml (22.5×10$^6$/ml) buffer (CliniMACS® PBS/EDTA+0.5% HSA) and transferred to a cell transfer bag connected to valve 10 and welded off the TS. A new TS510 was subsequently installed, primed (i.e. equilibrated using CliniMACS® PBS/EDTA+ 0.5% HSA, the cell bag connected to the TS and cell suspension was transferred to the CCU. Additionally, 500 µl of CD117-PE (Miltenyi Biotec; 130-099-672) mixed with 4.5 ml CliniMACS® PBS/EDTA+0.5% HSA in a Cryo-MACS freezing bag (Miltenyi-Biotec 200-074-400) was sterilely connected to the TS at valve 2 and transferred into the CCU (primary labeling). Cells were incubated at 4° C. for 15 min, then washed with CliniMACS® PBS/EDTA+ 0.5% HSA sedimented and resuspended in 20 ml Clini-MACS® PBS/EDTA+0.5% HSA. Thereafter, secondary labeling was conducted by transferring 2.27 ml Anti-PE MicroBeads (Miltenyi Biotec; 130-048-801) mixed with 2.73 ml CliniMACS® PBS/EDTA+0.5% HSA from a Cryo-MACS freezing bag (Miltenyi-Biotec 200-074-400) sterilely connected to the TS at valve 3 to the CCU. Cells were incubated at 4° C. for 10 min, then washed with Clini-MACS® PBS/EDTA+0.5% HSA sedimented and resuspended in 20 ml CliniMACS® PBS/EDTA+0.5% HSA and applied to the preequilibrated separation column. After column wash cells were eluted from the column and transferred to the Target Cell bag. Using this process a cell composition of $50 \times 10^6$ ventral midbrain dopaminergic progenitor cells could be retrieved at a purity of 80%.

What is claimed is:

1. An in vitro method for obtaining a cell population enriched for cells that have a protein expression profile characteristic of ventral midbrain patterned dopaminergic progenitor cells, the method comprising:
   a) differentiating a sample of a line of pluripotent and/or multipotent stem cells into a neural cell preparation that contains dopaminergic progenitor cells;
   b) dissociating the neural cell preparation into a suspension of individual cells;
   c) sorting the individual cells in the suspension using an antigen binding molecule specific for CD117 (c-KIT) into CD117 positive cells and CD117 negative cells; and
   d) harvesting the CD117 positive cells from step (c) to obtain said cell population;
   wherein at least 70% of the cells in the cell population harvested in step (d) have said protein expression profile characteristic of ventral midbrain patterned dopaminergic progenitor cells.

2. The method according to claim 1, wherein said method comprises additionally the step of depleting CD171 positive cells from said cell population by using an antigen binding molecule specific for the antigen CD171.

3. The method according to claim 1, wherein said pluripotent and/or multipotent stun cells are proliferated in a proliferation step before step (a).

4. The method according to claim 1, wherein said method is performed in a closed system.

5. The method according to claim 4, wherein said method is an automated method.

6. The method according to claim 1, wherein said antigen binding molecule specific for the CD117 antigen is an anti-CD117 antibody or antigen-binding fragment thereof.

7. The method according to claim 1, wherein step (c) is performed by fluorescent activated cell sorting or magnetic cell sorting.

8. The method according to claim 1, wherein said method comprises additionally the step of depleting pluripotent and/or multipotent stem cells from said CD117 positive cells by using an antigen binding molecule specific for a pluripotent and/or multipotent stem cell surface marker.

9. The method according to claim 8, wherein the step of depleting pluripotent and/or multipotent stem cells is performed by fluorescent activated cell sorting or magnetic cell sorting.

10. The method according to claim 8, wherein said antigen binding molecule specific for a pluripotent and/or multipotent stem cell marker is selected from the group consisting of SSEA4, UEA-1, SSEA-3, Tra-1-60, Tra-1-81, SSEA-5, CD90 and CD30.

11. The method according to claim 10, wherein said antigen binding molecule specific for a pluripotent and/or multipotent stem cell marker is SSEA4.

12. The method according to claim 1, wherein the ventral midbrain patterned dopaminergic progenitor cells are human or non-human primate cells.

13. The method according to claim 1, wherein said expression profile includes expression of forkhead box protein A2 (FoxA2).

14. The method according to claim 13, wherein said expression profile includes lack of expression of octamer-binding transcription factor 4 (Oct3/4).

15. The method according to claim 1, wherein said expression profile includes expression of FoxA2, orthodenticle homeobox 2 (Otx2) and nuclear receptor related 1 protein (Nurr1).

16. The method according to claim 1, wherein said line of pluripotent and/or multipotent stem cells is a line of embryonic stem cells (ESC) or a line of induced pluripotent stem cells (iPSC), and step (a) comprises culturing the sample on a cultivation matrix in the presence of differentiation and patterning factors for ventral midbrain patterned cells.

17. An in vitro method composing:
   a) obtaining a suspension of single cells from a preparation of dopaminergic progenitor cells differentiated from embryonic stein cells (ESC) or induced pluripotent stem cells (iPSC);
   b) specifically sorting cells in the suspension into CD117 positive and CD117 cells; and
   c) harvesting the CD117 positive cells from step (b);
   wherein at least 80% of the cells harvested in step (c) are positive for FoxA2, Otx2, and Nurr1.

18. The method according to claim 17, wherein the cells harvested in step (c) is a cell population enriched for ventral midbrain patterned dopaminergic progenitor cells.

19. The method according to claim 17, which is performed entirely in a closed cell processing system under GMP conditions,
   wherein step (b) comprises contacting cells in the suspension with antigen binding molecules specific for CD117 each coupled to a ferromagnetic particle, and retaining cells bearing a ferromagnetic particle in a magnetic field in the closed system while cells not bearing a ferromagnetic particle flow through;
   wherein step (c) comprises removing the magnetic field and recovering cells therefrom.

20. The method according to claim 19, further comprising compounding cells harvested in step (c) with one or more pharmaceutically acceptable carriers, diluents or excipients to form a pharmaceutical composition suitable for administration to a human subject.

21. The method according to claim 19, wherein $50 \times 10^6$ ventral midbrain patterned dopaminergic progenitor cells are retrieved from the closed system at a purity of at least 80%.

22. A plurality of cell populations comprising in separate containers in vitro:
   (I) a first cell population enriched for ventral midbrain patterned dopaminergic progenitor cells, obtained by differentiating a first sample of pluripotent or multipotent stem cells, and selecting CD117 (c-Kit) positive cells according to the method of claim 1,
wherein said pluripotent or multipotent stem cells are a line of embryonic stem cells (ESC) or induced pluripotent cells (iPSC); and (II) a second cell population, which is a second sample of the same ESC or iPSC in undifferentiated form, which is capable of being differentiated and enriched to obtain additional ventral midbrain patterned dopaminergic progenitor cells that are autologous to said first cell population.

23. The cell populations of claim 22, wherein the line is a line of embryonic stem cells (ESC).

24. The cell populations of claim 22, wherein the line is a line of induced pluripotent stem cells (iPSC).

* * * * *